(12) United States Patent
Woodward et al.

(10) Patent No.: US 7,491,383 B2
(45) Date of Patent: Feb. 17, 2009

(54) COMPOSITIONS HAVING ENHANCED PHARMACOKINETIC CHARACTERISTICS

(75) Inventors: David F. Woodward, Lake Forest, CA (US); Gyorgy Ambrus, Santa Ana, CA (US)

(73) Assignee: Allergan, Inc., Irvine, CA (US)

( * ) Notice: Subject to any disclaimer, the term of this patent is extended or adjusted under 35 U.S.C. 154(b) by 559 days.

(21) Appl. No.: 10/136,240

(22) Filed: May 1, 2002

(65) Prior Publication Data

US 2003/0017199 A1    Jan. 23, 2003

Related U.S. Application Data

(63) Continuation-in-part of application No. 09/847,935, filed on May 3, 2001.

(51) Int. Cl.
*A61K 31/74* (2006.01)
*A61K 9/00* (2006.01)
*A61K 31/505* (2006.01)
*A61K 31/495* (2006.01)

(52) U.S. Cl. .................. 424/78.08; 424/400; 514/272; 514/249

(58) Field of Classification Search ............. 424/78.08, 424/400; 514/272, 249, 222.8
See application file for complete search history.

(56) References Cited

U.S. PATENT DOCUMENTS

| | | | |
|---|---|---|---|
| 4,188,393 A | 2/1980 | Neumann | |
| 4,617,407 A | 10/1986 | Young et al. | |
| 4,629,621 A | 12/1986 | Snipes | |
| 4,683,325 A | 7/1987 | Frenette et al. | |
| 4,761,425 A | 8/1988 | Girard et al. | |
| 4,885,309 A | 12/1989 | Welton | |
| 5,093,356 A | 3/1992 | Girard et al. | |
| 5,118,493 A | 6/1992 | Kelley et al. | |
| 5,180,721 A * | 1/1993 | Burke ................ | 514/217.01 |
| 5,256,680 A | 10/1993 | Connor et al. | |
| 5,276,044 A | 1/1994 | Ambrus et al. | |
| 5,795,909 A | 8/1998 | Shashoua et al. | |
| 5,811,443 A | 9/1998 | DeSantis, Jr. et al. | |
| 5,834,470 A * | 11/1998 | Maurer ................ | 514/249 |
| 5,916,900 A | 6/1999 | Cupps et al. | |
| 5,922,744 A | 7/1999 | Harrison et al. | |
| 5,962,462 A | 10/1999 | Mills et al. | |
| 6,117,871 A * | 9/2000 | Maurer et al. ......... | 514/249 |
| 6,242,442 B1 * | 6/2001 | Dean et al. ........... | 514/222.8 |
| 6,255,502 B1 | 7/2001 | Penkler et al. | |
| 6,258,350 B1 * | 7/2001 | Mallick .............. | 424/78.04 |
| 6,294,553 B1 * | 9/2001 | Gil et al. ............. | 514/314 |
| 6,294,563 B1 | 9/2001 | Garst | |
| 6,358,935 B1 | 3/2002 | Beck et al. | |
| 6,465,464 B2 * | 10/2002 | Wheeler et al. ........ | 514/249 |
| 6,627,210 B2 | 9/2003 | Olejnik et al. | |
| 6,673,802 B2 * | 1/2004 | Castelhano et al. ..... | 514/263.2 |
| 2001/0056116 A1 | 12/2001 | Shashoua | |
| 2005/0191245 A1 | 9/2005 | Adams et al. | |

FOREIGN PATENT DOCUMENTS

| | | |
|---|---|---|
| DE | 3309765 | 9/1984 |
| EP | 0305726 | 3/1989 |
| EP | 0426390 | 5/1991 |
| JP | 11-130656 | 10/1997 |
| WO | WO 9744063 | 11/1997 |
| WO | WO 00/33818 | 6/2000 |
| WO | 00/44355 | 8/2000 |
| WO | WO 0205853 | 1/2002 |
| WO | WO 02089804 | 11/2002 |

OTHER PUBLICATIONS

French Republic Patent Application No. 75 00325, filed Jan. 1975.
Japanese Patent Application Kokai No. S62-48618, Publication Date Mar. 3, 1981.
Database Derwent on West, DE 3309765 A, Hanssler et al. (Abstract).
Database Derwent on West, FR 2272684 A (Abstract).
Database Derwent on West, JP 62048618 A (Abstract).
"Effects of Pretreatment With Mydriatics on Intraocular Penetration of 0.1% Pranoprofen", JNP J Opthalmol, vol. 37: 47-55, 1993, Ogawa et al.
Literature Search, "Ion Pair Complex Formulations" May 18, 2000, Requester: D.F. Woodward, Searcher: C.H. O'Donohue, 22 Pages.
"The Possibility of Lidocaine Ion Pair Absorption Through Excised Hairless Mouse Skin" Skin Pharmacol, 1992:5:160-170, Robert A. Nash et al.
"Protection by ITF 1300, a Heparin Ion-Pair Complex, Against Arrhythmias Induced by Regional Ischemia and Reperfusion in the Isolated Rat Heart:Possible Mechanism of Action", Journal of Cardiovascular Pharmacology, 25:643-651, 1995, Curtis et al.
Internet Brochure: Excipients—"Metolose", Shin-Etsu Chemical Co., Ltd., http://www.rwunwin.co.uk/excipients/met.htm, Feb. 27, 2006.

* cited by examiner

*Primary Examiner*—Michael G Hartley
*Assistant Examiner*—Blessing M Fubara
(74) *Attorney, Agent, or Firm*—Allergan, Inc.; Martin Voet; John E. Wurst

(57) ABSTRACT

Compositions comprising a therapeutic component and an efficacy enhancing component, that enhances the pharmacokinetic disposition of the therapeutic component, are disclosed. The therapeutic component may include an alpha-2-adrenergic agonist and the efficacy enhancing component may include fatty acids. In one embodiment, the therapeutic component and the efficacy enhancing component form a complex.

18 Claims, No Drawings

COMPOSITIONS HAVING ENHANCED PHARMACOKINETIC CHARACTERISTICS

RELATED APPLICATION

This application is a continuation in part of U.S. patent application Ser. No. 09/847,935 filed May 3, 2001, the disclosure of which is incorporated herein in its entirety by reference.

BACKGROUND OF THE INVENTION

The present invention relates to compositions containing therapeutic components, hereinafter TCs, for example, alpha-2-adrenergic agonists. More particularly, the invention relates to such compositions including such TCs, and advantageously one or more other components, in which compositions the TCs preferably have enhanced pharmacokinetic characteristics.

A TC includes any chemical entity, such as a compound, an ion, a complex and the like, which is effective to act on and/or bind to receptors and provide a therapeutic effect. The TC may be an agonist, an antagonist, precursors thereof, metabolites thereof and combinations thereof.

A continuing challenge in providing compositions having TCs is to be able to render such compositions more effective. One way to render the TCs more effective is to enhance their pharmacokinetic dispositions. For example, the dispensed or administered TCs should advantageously be permeable through lipid cell membranes so that the agonist may reach the target receptor to impart a therapeutic effect. One possible reason for why certain TCs permeate poorly through a lipid membrane is that these components may be charged ions at physiological pH.

Although the term "enhancement of pharmacokinetic disposition" as used herein may mean an enhancement in permeability, an enhancement of pharmacokinetic disposition may also mean an enhancement in, for example, bioavailability, sequestration and/or release characteristics of the TCs.

Ion pairing, or complexation, between cations and anions to enhance the movement of ionizable molecules across biologic membranes has been suggested. Nash et al. *Skin Pharmacol* 5:160-170 (1992) and Ogawa et al. *Jpn J Ophthalmol* 37:47-55 (1993). However, prior ion complex systems may be inappropriate for use to deliver TCs to certain biological environments, for example, the ophthalmic environment.

There continues to be a need for new compositions that increase the efficacy of therapeutic components.

SUMMARY OF THE INVENTION

New TC-containing compositions have been discovered. In accordance with the invention, the present compositions contain certain materials which are effective in enhancing the efficacy of the TCs of the compositions. Without limiting the invention to any particular theory or mechanism of operation, it is believed that the efficacy of the TCs is enhanced because of improved pharmacokinetics, for example, increased permeability of the TCs through lipid bilayers. In one embodiment, these materials enhance the bioavailability of the TCs in the eye. Preferably, the materials are able to enhance the pharmacokinetics of the TCs under physiological conditions, for example at pHs of about 6.5 to about 9.

The TCs are advantageously ionized or ionizable at physiological pHs, for example, about pH 6.0 to about pH 9.0. In one embodiment, the TCs are ionized or ionizable at about pH 7.

TCs employed in the present compositions include those compounds, mixtures of compounds, mixtures of other materials, which are useful to provide a therapeutic benefit or effect when administered to a patient, e.g. a human patient. The TCs useful in this invention include, without limitation, NMDA antagonists, antibacterials, antihistamines, decongestants, antiinflammatory, antiparasitics, miotics, anticholinergics, adrenergics, antivirals, local anesthetics, antifungals, amoebicidals, trichomonocidals, analgesics, mydriatics, antiglaucoma drugs, neuroprotective agents, anti-augiogenic agents, ophthalmic diagnostic agents, ophthalmic agents used as adjuvants in surgery, chelating agents, antineoplastics, antihypertensives, muscle relaxants, diagnostics and the like and mixtures thereof. Specific examples of such TCs are conventional and well known in the art.

The TCs may include alpha-2-adrenergic agonists. Alpha-2-adrenergic agonists include imino-imidazolines, imidazolines, imidazoles, azepines, thiazines, oxazolines, guanidines, catecholamines, biologically compatible salts and esters and mixtures thereof. The alpha-2-adrenergic agonist may include quinoxaline components. Quinoxaline components include quinoxaline, biologically compatible salts thereof, esters thereof, other derivatives thereof and the like, and mixtures thereof. Non-limiting examples of quinoxaline derivatives include (2-imidozolin-2-ylamino) quinoxaline, 5-bromo-6-(2-imidozolin-2-ylamino) quinoxaline, and biologically compatible salts thereof and esters thereof, for example, the tartrate of 5-bromo-6-(2-imidozolin-2-ylamino) quinoxaline, and the like and mixtures thereof. Hereinafter, 5-bromo-6-(2-imidozolin-2-ylamino) quinoxaline is referred to as "brimonidine", and the tartrate of 5-bromo-6-(2-imidozolin-2-ylamino) quinoxaline is referred to as "brimonidine tartrate."

The alpha-2-adrenergic agonists, such as those listed above, may be specific for the alpha-2A-adrenergic receptors, alpha-2B-adrenergic receptors and/or alpha-2D-adrenergic receptors or any combination thereof.

Materials which enhance the pharmacokinetics of the TCs include efficacy enhancing components, hereinafter EECs. In one embodiment, the EEC includes fatty acids, saturated and/or unsaturated. The fatty acids of the present invention may have more than 12 carbons, for example docosahexanoic acid and linolenic acid. In one embodiment, the fatty acids of the present invention comprise about 12 carbons to about 26 carbons. In another embodiment, the fatty acids of the present invention comprise about 16 carbons to about 24 carbons. In one embodiment, the EECs themselves are effective to provide at least one therapeutic effect.

The TC and the EEC form and/or are present in the form of a complex in the compositions of the present invention. In one embodiment, the TC and the EEC form a complex in solution, for example, a complex may be formed in a solution at a pH of about 5 to about 9, for example, about pH 7 to about pH 9. In one embodiment, the EEC and the TC form a complex that is an ion pair, for example, in an aqueous component. In one embodiment, the TC and EEC are able to form a complex present as a separate phase, for example a salt-like material and or oil phase, outside of a solution.

The present compositions may include carrier components. In one embodiment, the compositions have pHs of about 7 or greater. For example, the compositions may have pHs of between about 7 and about 9, and preferably are ophthalmically acceptable.

In a useful embodiment, a solubilizer component may be included in the present compositions. The solubilizer component is present in an amount effective to enhance the solubility of the complexes in the present compositions. Although any suitable solubilizer component may be employed, the solubilizer component is advantageously nonionic. Non-limiting examples of useful solubilizer components include poly(oxyethylene)-poly(oxypropylene) block polymers, polysorbate 80, polyvinyl alcohol, polyvinylpyrrolidine, hydroxypropylmethyl cellulose and the like and mixtures thereof.

Still further in accordance with the invention, the present compositions may include an effective amount of a nonionic tonicity component. Nonlimiting examples of useful nonionic tonicity components are mannitol, glycerine and mixtures thereof.

The EEC and TC advantageously are present in amounts so that the ratio of electrical charge from the EEC to electrical charge from the TC is in range of about 0.9 to about 1.5. In a preferred embodiment, the ratio of electrical charge from the EEC to electrical charge from the TC is in a range of about 0.95 to about 1.4, for example, about 1.0 to about 1.3.

The present compositions may include a buffer component. Although any suitable buffer component may be employed, it is advantageous to employ a buffer component which is effective at reduced concentrations, for example, to assist in reducing the ionic concentration in the present compositions. In one embodiment, the buffer component is present in a range of about 0.001 molar or about 0.005 molar to about 0.05 molar about 0.1 molar. In one useful embodiment, the buffer component is a phosphate buffer component.

Any feature or combination of features described herein are included within the scope of the present invention provided that the features included in any such combination are not mutually inconsistent as will be apparent from the context, this specification, and the knowledge of one of ordinary skill in the art.

Additional advantages and aspects of the present invention are apparent in the following detailed description and claims.

DETAILED DESCRIPTION OF THE INVENTION

Compositions comprising therapeutic components, TCs, and efficacy enhancing components, EECs, are provided. The EECs employed in the present compositions may be effective in enhancing the pharmacokinetics of the TCs. For example, the EEC may enhance the therapeutic effect of the therapeutic component. In one embodiment, the present compositions may further include liquid carrier components and have the characteristics of liquid, for example, aqueous liquid, solutions.

In one embodiment, the TC and the EEC form complexes. The complexes formed may be a "loose" ion pair or a "tight" ion pair. In one useful embodiment, the complex of the present invention is a "tight" ion pair. For example, the complexes of this invention are adequately "tight" as to not dissociate in high dielectric constant solvent, such as water or aqueous solutions. One advantage of such a "tight" ion pair complex is that the complex may be contained in an aqueous solution, for example saline, which may be used in an ophthalmic environment.

In one embodiment, the complex is able to dissociate under certain conditions. For example, after the complex crosses the lipid layer, the TC may activate a targeted molecule more effectively if it is not complexed to an EEC. Therefore, in one embodiment, the TC and the EEC exist as a complex for the purpose of enhancing the pharmacokinetic disposition of the TC and thereafter dissociate to allow the TC to act more effectively at a receptor.

In one embodiment, a single TC may form a complex with more than one EEC, for example two or three EECs. In another embodiment, a single EEC may form a complex with more than one TC, for example two or three TCs.

In one embodiment, a single TC molecule may form a complex with one or more EEC molecules, for example, one, two or three EEC molecules may form a complex with one TC molecule. In another embodiment, a single EEC molecule may form a complex with more than one TC molecules, for example, two or three TC molecules may form a complex with one EEC molecule.

The presently useful TCs preferably are chosen to benefit from the presence of the EECs. In general, the TCs are provided with enhanced ability to cross a lipid membrane when they complex with the EECs. In one embodiment, the TCs are basic molecules. In another embodiment, the TCs are cations.

Examples of TCs which may be included in the present compositions include, but are not limited to, NMDA antagonists; antibacterial substances such as beta-lactam antibiotics, such as cefoxitin, n-formamidoylthienamycin and other thienamycin derivatives, tetracyclines, chloramphenicol, neomycin, carbenicillin, colistin, penicillin G, polymyxin B, vancomycin, cefazolin, cephaloridine, chibrorifamycin, gramicidin, bacitracin and sulfonamides; aminoglycoside antibiotics such as gentamycin, kanamycin, amikacin, sisomicin and tobramycin; nalidixic acid and its analogs such as norfloxacin and the antimicrobial combination fluoroalanine/pentizidone, nitrofurazones and analogs thereof; antihistaminics and decongestants such as pyrilamine, chlorpheniramine, tetrahydrazoline, antazoline and analogs thereof; mast-cell inhibitors of histamine release, such as cromolyn; anti-inflammatories such as cortisone, hydrocortisone, hydrocortisone esters, betamethasone, dexamethasone, dexamethasone sodium phosphate, prednisone, methylprednisolone, medrysone, fluorometholone, prednisolone, prednisolone sodium phosphate, triamcinolone, indainethacin, sulindac, its salts and its corresponding sulfides, and analogs thereof; miotics and anticholinergics such as echothiophate, pilocarpine, physostigmine salicylate, diisopropylfluorophosphate, epinephrine, dipivaloylepinephrine, neostigmine echothiopate iodide, demecarim bromide, carbamoyl choline chloride, methacholine, bethanechol, and analogs thereof; mydriatics such as atrophine, homatropine, scopolamine, hydroxyamphetamine, ephedrine, cocaine, tropicamide, phenylephrine, cyclopentolate, oxyphenonium, eucatropine; and the like and mixtures thereof. Other TCs are: antiglaucama drugs, for example, timolol, and especially its maleic salt and R-timolol and a combination of timolol or R-timolol with pilocarpine; other adrenergic agonists and/or antagonists such as epinephrine and an epinephrine complex, or prodrugs such as bitartrate, borate, hydrochloride and dipivefrine derivatives; carbonic anhydrase inhibitors such as acetazolamide, dichlorphenamide, 2-(p-hydroxyphenyl)-thiothiophene-sulfonamide, 6-hydroxy-2-benzothiazolesulfonamide, and 6-pivaloyloxy-2-benzothiazolesulfonamide; antiparasitic compounds and/or anti-protozoal compounds such as ivermectin, pyrimethamine, trisulfapidimidine, clindamycin and corticosteroid preparations; compounds having antiviral activity such as acyclovir, 5-iodo-2'-deoxyuridine (IDU), adenosine arabinoside (Ara-A), trifluorothymidine, interferon, and interferon-inducing agents such as poly I:C; antifungal agents such as amphotericin B, nystatin, flucytosine, natamycin and miconazole; anesthetic agents such as etidocaine cocaine, benoxinate, dibucaine hydrochloride, dyclonine hydrochloride, naepaine, phenacaine hydrochloride, piperocaine, proparacaine hydrochloride, tetracaine hydrochloride, hexylcaine, bupivacaine, lidocaine, mepivacaine and prilocaine; ophthalmic diagnostic agents, such as: (a) those used to examine the retina such as sodium fluorescein, (b) those used to examine the conjunctiva, cornea and lacrimal apparatus, such as fluorescein and rose bengal and (c) those used to examine abnormal pupillary responses such as methacholine, cocaine, adrenaline, atropine, hydroxyamphetamine and pilocarpine; ophthalmic agents used as adjuncts in surgery, such as alpha-chymotrypsin and hyaluronidase; chelating agents such as ethylenediaminetetraacetic acid (EDTA) and deferoxamine; immunosuppressants and anti-metabolites such as methotrexate, cyclophosphamide, 6-mercaptopurine and azathioprine and combinations of the compounds mentioned above, such as antibiotics/antiinflammatories combinations such as the combination of neomycin sulfate and dexamethasone sodium phosphate and combinations concomitantly used for treating glaucoma, for example, a combination of timolol maleate and aceclidine; and the like and mixtures thereof.

In a preferred embodiment, the useful TCs include adrenergic agonists. The adrenergic agonists may be molecules containing amines. Also, the adrenergic agonists may be amine-containing molecules with pKa's of greater than 7, preferably about 7 to about 9.

In one embodiment, the useful TCs include alpha-adrenergic agonists. Examples of alpha-adrengergic agonists include, but not limited to, adrafinil, adrenolone, amidephrine, apraclonidine, budralazine, clonidine, cyclopentamine, detomidine, dimetofrine, dipivefrin, ephedrine, epinephrine, fenoxazoline, guanabenz, guanfacine, hydroxyamphetamine, ibopamine, indanazoline, isometheptene, mephentermine, metaraminol, methoxamine, methylhexaneamine, metizolene, midodrine, naphazoline, norepinephrine, norfenefrine, octodrine, octopamine, oxymetazoline, phenylephrine, phenylpropanolamine, phenylpropylmethylamine, pholedrine, propylhexedrine, pseudoephedrine, rilmenidine, synephrine, tetrahydrozoline, tiamenidine, tramazoline, tuaminoheptane, tymazoline, tyramine, xylometazoline, and the like and mixtures thereof.

In one useful embodiment, the TCs include alpha-2-adrenergic agonists. As used herein, the term "alpha-2 adrenergic agonist" includes chemical entities, such as compounds, ions, complexes and the like, that may produce a net sympatholytic response, resulting in increased accommodation, for example, by binding to presynaptic alpha-2 receptors on sympathetic postganglionic nerve endings or, for example, to postsynaptic alpha-2 receptors on smooth muscle cells. A sympatholytic response is characterized by the inhibition, diminishment, or prevention of the effects of impulses conveyed by the sympathetic nervous system. The alpha-2 adrenergic agonists of the invention may bind to the alpha-2 adrenergic receptors presynaptically, causing negative feedback to decrease the release of neuronal norepinephrine. Additionally, they also may work on alpha-2 adrenergic receptors postsynaptically, inhibiting beta-adrenergic receptor-stimulated formation of cyclic AMP, which contributes to the relaxation of the ciliary muscle, in addition to the effects of postsynaptic alpha-2 adrenergic receptors on other intracellular pathways. Activity at either pre- or postsynaptic alpha-2 adrenergic receptors may result in a decreased adrenergic influence. Decreased adrenergic influence results in increased contraction resulting from cholinergic innervations. Alpha-2 adrenergic agonists also include compounds that have neuroprotective activity. For example, 5-bromo-6-(2-imidozolin-2-ylamino) quinoxaline is an alpha-2-adrenergic agonist which has a neuroprotective activity through an unknown mechanism. Without limiting the invention to the specific groups and compounds listed, the following is a list of representative alpha-2 adrenergic agonists useful in this invention: imino-imidazolines, including clonidine, apraclonidine; imidazolines, including naphazoline, xymetazoline, tetrahydrozoline, and tramazoline; imidazoles, including detomidine, medetomidine, and dexmedetomidine; azepines, including B-HT 920 (6-allyl-2-amino-5,6,7,8 tetrahydro-4H-thiazolo[4,5-d]-azepine and B-HT 933; thiazines, including xylazine; oxazolines, including rilmenidine; guanidines, including guanabenz and guanfacine; catecholamines and the like.

Particularly useful alpha-2-adrenergic agonists include quinoxaline components. In one embodiment, the quinoxaline components include quinoxaline, derivatives thereof and mixtures thereof. The derivatives of quinoxaline include, without limitation, (2-imidozolin-2-ylamino) quinoxaline. In one embodiment, the derivatives of quinoxaline include 5-halide-6-(2-imidozolin-2-ylamino) quinoxaline. The "halide" of the 5-halide-6-(2-imidozolin-2-ylamino) quinoxaline may be a fluorine, a chlorine, an iodine, or preferably, a bromine, to form 5-bromo-6-(2-imidozolin-2-ylamino) quinoxaline.

Other useful quinoxaline derivatives are well known. For example, useful derivatives of a quinoxaline include the ones disclosed by Burke et al U.S. Pat. No. 5,703,077. See also Danielwicz et al 3,890,319. Each of the disclosures of Burke et al and Danielwicz et al is incorporated in its entirety by reference herein.

The quinoxaline and derivatives thereof, for example brimonidine, are amine-containing and preferably have pKa's of greater than 7, preferably about 7.5 to 9.

Analogs of the foregoing compounds that function as alpha-2 adrenergic agonists also are specifically intended to be embraced by the invention.

The alpha-2-adrenergic agonists, for example the ones listed above, may be effective toward activating one or more of alpha-2A-adrenergic receptors, alpha-2B-adrenergic receptors and alpha-2D-adrenergic receptors.

In one embodiment, the composition of the present invention includes a TC other than an alpha-2-adrenergic agonist. For example, a composition in accordance with the present invention may include a TC which is not a quinoxaline such as 5-bromo-6-(2-imidozolin-z-ylamino) quinoxaline (brimonidine).

Other useful TCs include ocular hypotensive agents (Woodward et al U.S. Pat. No. 5,688,819), pyranoquinolinone derivatives (Cairns et al U.S. Pat. No. 4,474,787), compounds having retinoid-like activities (Chandraratna U.S. Pat. No. 5,089,509), ketorolac/pyrrole-l-carboxylic acids (Muchowski et al U.S. Pat. No. 4,089,969), ofloxacins/benzoxazine derivatives (Hayakawa et al U.S. Pat. No. 4,382,892), memantines (Lipton et al U.S. Pat. No. 5,922,773). The disclosure of each of these patents is incorporated in its entirety herein by reference.

In one useful embodiment, the amount of TC in the present composition is in the range of about 0.05% to about 30% (w/v). The amount of TC may be in the range of about 0.1% (w/v) to about 10% (w/v). For example, the amount of TC may be in the range of about 0.1% (w/v) to about 0.6% (w/v). In one embodiment, the TC is an adrenergic agonist and is present in the composition in the range of about 0.1% (w/v) to about 0.6% (w/v), for example, about 0.13%.

Any suitable EECs may be employed in accordance with the present invention. In one embodiment, the EECs are acidic molecules. In another embodiment, the EECs are anions. In one embodiment, EECs include fatty acids or derivatives thereof. The fatty acids may possess a long hydrophobic carbon chain and a terminal carboxyl group. The chain may be saturated, or it may have one or more double bonds. Moreover, fatty acids may contain triple bonds. Fatty acids may differ, for example, in length and in the number and position of their unsaturated bonds. Non-limiting examples of saturated fatty acids include lauric acid, myristic, palmitic, stearic, arachidic, lignoceric, derivatives thereof, and the like and mixtures thereof. Non-limiting examples of unsaturated fatty acids include palmitoleic, oleic, linoleic, linolenic, arachidonic, derivatives thereof, and the like and mixtures thereof. Other examples of some unusual fatty acids include trans-Vaccenic acid, lactobacillic, tuberculostearic, cerebronic, derivatives thereof, and the like and mixtures thereof.

In one embodiment, the EEC includes a docosahexanoic acid. In another embodiment, the EEC includes a linolenic acid.

In one embodiment, the fatty acids of the present invention comprises about 12 carbon atoms to about 26 carbon atoms. In another embodiment, the fatty acids of the present invention comprises about 16 carbon atoms to about 24 carbons.

In one embodiment, the EEC has a direct therapeutic effect. For example, an EEC may include eicosanoids, such as prostanoids. A prostanoid is any group of complex fatty acids derived from arachidonic acid, being 20 carbon in length with an internal 5 or 6 carbon ring, for example prostaglandin, protanoic acid and thromboxanes. Prostanoids are known to reduce intra-ocular pressure. In one embodiment, a composition according to the invention comprises a complex having a TC and a therapeutically effective EEC. For example, a composition according to the present invention may comprise a complex of an adrenergic agonist and a prostanoid. Both the adrenergic agonist and the prostanoid may act, via different mechanisms, to provide an additive therapeutic effect, for example, to reduce intra-ocular pressure. The EEC may exert its therapeutic effects when it is still bound to a complex, or the EEC may exert its effects when it is free from the complex.

Although fatty acids are preferred as counter ions to form complexes with TCs, such as the adrenergic agonists, other molecules may be used as counter ions to form complexes with the TCs. In one embodiment, the complexes formed are able to enhance the movement of the TCs across lipid layers. In one embodiment, these complexes are able to solubilize the TCs in solution, preferably solutions with pHs of about 7 to about 10.

EECs other than fatty acids include anionic polymers derivatives thereof, and the like and mixtures thereof. In one embodiment, the anionic polymers are added to a solution containing TCs to form a complex with the TCs therein. Preferably, the anionic polymer is ophthalmically acceptable at the concentrations used. Additionally, the anionic polymer may include one or more, for example, two (2) or three (3), anionic (or negative) charges. Furthermore, anionic polymers with more than 1 anionic site may be employed to reduce the osmotic pressure of a solution containing TCs. For example, a solution having a complex wherein several TCs complex to a single anionic polymer has a lower osmotic pressure than a similar solution wherein the TCs are not complexed.

Examples of anionic polymers which may have multiple anionic charges include:
  metal carboxymethylstarchs
  metal carboxymethylhydroxyethylstarchs
  hydrolyzed polyacrylamides and polyacrylonitriles heparin
  homopolymers and copolymers of one or more of:
    acrylic and methacrylic acids
    metal acrylates and methacrylates
    alginic acid
    metal alginates
    vinylsulfonic acid
    metal vinylsulfonate
    amino acids, such as aspartic acid, glutamic acid and the like
    metal salts of amino acids
    p-styrenesulfonic acid
    metal p-styrenesulfonate
    2-methacryloyloxyethylsulfonic acids
    metal 2-methacryloyloxethylsulfonates
    3-methacryloyloxy-2-hydroxypropylsulfonic acids
    metal 3-methacryloyloxy-2-hydroxypropylsulfonates
    2-acrylamido-2-methylpropanesulfonic acids
    metal 2-acrylamido-2-methylpropanesulfonates
    allylsulfonic acid
    metal allylsulfonate and the like
  cellulose derivatives:
    carboxymethylcelluloses
    metal carboxymethylhydroxyethylcelluloses
    hydroxypropylmethylcelluloses In another embodiment, the anionic polymers include anionic polysaccharides which tend to exist in ionized forms at higher pHs, for example, pHs of about 7 or higher. The following are some examples of anionic polysaccharides which may be employed in accordance with this invention.

Polydextrose is a randomly bonded condensation polymer of dextrose which is only partially metabolized by mammals. The polymer may contain a minor amount of bound sorbitol, citric acid, and glucose. Chondroitin sulfate also known as sodium chondroitin sulfate is a mucopolysaccharide found in human tissue, specifically cartilage, bones, tendons, ligaments, and vascular walls. This polysaccharide has been extracted and purified from the cartilage of sharks. Carrageenan is a linear polysaccharide having repeating galactose units and 3,6 anhydrogalactose units, both of which can be sulfated or nonsulfated, joined by alternating 1-3 and beta 1-4 glycosidic linkages. Carrageenan is a hydrocolloid which is heat extracted from several species of red seaweed and irish moss. Maltodextrins are water soluble glucose polymers which are formed by the reaction of starch with an acid and/or enzymes in the presence of water. Other anionic polysaccharides found useful in the present invention are hydrophilic colloidal materials and include the natural gums such as gellan gum, alginate gums, i.e., the ammonium and alkali metal salts of alginic acid and mixtures thereof. In addition, chitosan, which is the common name for deacetylated chitin is useful. Chitin is a natural product comprising poly-(N-acetyl-D-glucosamine). Gellan gum is produced from the fermentation of *Pseudomonas elodea* to yield an extracellular heteropolysaccharide. The alginates and chitosan are available as dry powders from Protan, Inc., Commack, N.Y. Gellan gum is available from the Kelco Division of Merk & Co., Inc., San Diego, Calif. Generally, the alginates can be any of the water-soluble alginates including the alkali metal alginates, such as sodium, potassium, lithium, rubidium and cesium salts of alginic acid, as well as the ammonium salt, and the soluble alginates of an organic base such as mono-, di-, or tri-ethanolamine alginates, aniline alginates, and the like. Generally, about 0.2% to about 1% by weight and, preferably, about 0.5% to about 3.0% by weight of gellan, alginate or chitosan ionic polysaccharides, based upon the total weight of the composition, are used to obtain the gel compositions of the invention.

The anionic polysaccharides may be cyclized. The cyclized anionic polysaccharides may include less than ten monomer units. For example, the cyclized polysaccharides include less than six monomer units.

In one embodiment, a particularly useful group of cyclized anionic polysaccharides includes the cyclodextrins. Examples of the cyclodextrin group include, but are not limited to: α-cyclodextrin, derivatives of α-cyclodextrin, β-cyclodextrin, derivatives of β-cyclodextrin, γ-cyclodextrin, derivatives of γ-cyclodextrin, carboxymethyl-β-cyclodextrin, carboxymethyl-ethyl-β-cyclodextrin, diethyl-β-cyclodextrin, dimethyl-β-cyclodextrin, methyl-β-cyclodextrin, random methyl-β-cyclodextrin, glucosyl-β-cyclodextrin, maltosyl-β-cyclodextrin, hydroxyethyl-β-cyclodextrin, hydroxypropyl-β-cyclodextrin, sulfobutylether-β-cyclodextrin, and the like and mixtures thereof. Sulfobutylether-β-cyclodextrin is a preferred cyclized anionic polyasaccharide in accordance with the present invention. It is advantageous that the EECs, including the above mentioned cyclodextrins, employed in this invention be, at the concentration employed, non-toxic to a mammal, for example a human. As used herein, the term "derivatives," as it relates to a cyclodextrin, means any substituted or otherwise modified compound which has the characteristic chemical structure of a cyclodextrin sufficiently to function as a cyclodextrin component, for example, to enhance the solubility and/or stability of active components and/or reduce unwanted side effects of the active components and/or to form inclusive complexes with active components, as described herein.

Although cyclodextrins and/or their derivatives may be employed as EECs, one embodiment of the invention may include EECs other than cyclodextrins and/or their derivatives.

A particularly useful class of anionic polymer includes anionic cellulose derivatives. Anionic cellulose derivatives include metal carboxymethyl-celluloses, metal carboxymethylhydroxyethylcelluloses and hydroxypropylmethylcelluloses and derivatives thereof.

In one embodiment, a complex of a TC and a EEC may exist as a salt-like material and/or an oil phase outside of a solution. For example, a complex of brimonidine and linoleic acid may be a powder. Furthermore, this complex may be added to a solution, for example a saline solution. Preferably, the TC and the EEC still remain as a complex. In one embodiment, the solution containing the complex, for example a complex of brimonidine and linoleic acid, is administered to the eye to treat glaucoma. In one embodiment, the complex remains intact at the site where the therapeutic component may exert a therapeutic effect. In a preferred embodiment, the complex dissociates at or near the site where the therapeutic component may exert a therapeutic effect. For example, a complex of brimonidine and linolenic acid may dissociate to release brimonidine at or near the ciliary body in the eye, wherein the brimonidine can act on receptors located on the ciliary body to reduce the production of aqueous solutions, thereby treating glaucoma.

In another embodiment, a EEC is added to a solution containing TC to form a complex with the TC therein. In one embodiment, the complex is formed only in solution. The amount of EEC added is such that the pharmacokinetics of the TC is at least somewhat increased. Such amount should be effective to perform the desired function or functions in the present composition and/or after administration to the human or animal. In one embodiment, one or more EECs, which may include an anionic polymer, are present in an amount sufficient to form a complex with at least a portion or substantially all of the TC present in a present composition. Advantageously, the EEC is present in an effective amount, but less than the amount required to form an emulsion, for example, with the water present in the composition. In one useful embodiment, the complex is not present in an emulsion, for example, an EEC/water emulsion. The present compositions preferably includes no emulsions, for example, as described herein. At least about 10% or about 30% or about 50% or about 70% of the TC in the present compositions preferably is present in the form of a complex with the EEC(s). More preferably, more preferably about 80% or about 90% to about 100% of the TC present is in such a complex.

In one useful embodiment, the amount of EEC, for example, an anionic polymer, in the present composition is in the range of about 0.1% to about 30% (w/v) or more of the composition. For example, the amount of EEC is in the range of about 0.2% (w/v) to about 10% (w/v). In one embodiment, the amount of EEC is in the range of about 0.2% (w/v) to about 0.6% (w/v). In another embodiment, the EEC is carboxymethylcellulose and is present in the composition in the range of about 0.2% (w/v) to about 0.6% (w/v). One useful concentration of carboxymethylcellulose in the present compositions is about 0.5%.

In one embodiment, the TCs and the EECs form complexes at pHs of greater than 7. Preferably, the TCs and the EECs form complexes at pHs between about 7 to about 10.

Without wishing to limit the present invention to any particular theory or mechanism of operation, it is believed that at least one element which contributes to complex stabilization and/or inhibition of complex disassociation is an interaction of the non-polar or hydrophobic hydrocarbon portion or tail of the EEC with the TC. This interaction may act in combination with the ionic interaction between the EEC and the TC to enhance complex stabilization and/or inhibit complex disassociation. This interaction may also be involved in enhancing complex formation. The effects of the hydrophobic interaction and ionic interaction may be synergistic in nature.

Compositions of the present invention may advantageously include solubilizer components which at least assist in maintaining the TC-EEC complex in solution or dispersed in the composition. For example, a solubilizer component may be useful to maintain the TC-EEC complex in solution under conditions which, in the absence of a solubilizer component, would result in insolubility and/or precipitation of the TC-EEC complex. These conditions include one or more of certain pH values, certain concentrations of the TC and/or EEC, certain ionic concentrations and the like. The presence of a solubilizer component preferably reduces the solubility sensitivity of the present complexes to these conditions and allows for more flexibility in formulating the present compositions.

The inclusion of ions or ionic species in the present compositions may weaken the bonding between the TC and the EEC in the complexes, disadvantageously resulting in a lowered concentration of intact TC-EEC complexes. Therefore, in one useful embodiment, the solubilizer component is nonionic to reduce the ionic concentration in the present compositions and still provide the benefits to be attained from the solubilizer component. Examples of nonionic solubilizer components include, without limitation, poly(oxyethylene)-poly(oxypropylene) block polymers, polysorbate 80, polyvinyl alcohol, polyvinylpyrrolidine, hydroxypropylmethyl cellulose and the like and mixtures thereof.

In one embodiment, the complex according to the present invention may serve as a delay release system for the TCs and/or the EECs. For example, a TC may be pharmacologically inactive when it is part of a complex. However, as the complex disassociates, for example, slowly disassociates over time in a biological environment, it releases, for example, slowly releases the TC. A slow and/or delayed release of a pharmacologically active TC may be advantageous. For example, such delayed release may be helpful in providing appropriate dosing.

In one embodiment, the complexation of TCs with EECs may further help to solubilize the TCs in solution and preferably reduces irritation when the TCs are administered to sensitive tissues. For example, an eye drop solution having a pH of about 7 may contain insoluble TC ions, such as brimonidine tartrate ions. If such a solution is administered to the eye, a sensitive tissue, the insoluble TC ions may cause discomfort and irritation. However, a complex of TC and EEC may help solubilize the TC in such a solution. In one embodiment, the solution containing a solubilized TC results in less irritation as the solution is applied to a sensitive tissue, for example the eye. In a more preferred embodiment, the solution containing solubilize TC results in little or no irritation when the solution is administered to a sensitive tissue.

In one embodiment, the compositions may also is include preservative components or components which assist in the preservation of the composition. The preservative components selected so as to be effective and efficacious as preservatives in the present compositions, that is in the presence of EECs, and preferably have reduced toxicity and, more preferably, substantially no toxicity when the compositions are administered to a human or animal.

Preservatives or components which assist in the preservation of the composition which are commonly used in pharmaceutical compositions are often less effective when used in the presence of solubilizing agents or solubilizing component. In certain instances, this reduced preservative efficacy can be compensated for by using increased amounts of the preservative. However, where sensitive or delicate body tissue is involved, this approach may not be available since the preservative itself may cause some adverse reaction or sensitivity in the human or animal, to whom the composition is administered.

Preferably, the present preservative components or components which assist in the preservation of the composition, for example, the TCs and/or EECs therein, are effective in concentrations of less than about 1% (w/v) or about 0.8% (w/v) and may be 500 ppm (w/v) or less, for example, in the range of about 10 ppm(w/v) or less to about 200 ppm(w/v). Preservative components in accordance with the present invention preferably include, but are not limited to, those which form complexes with the anionic polymer, or EEC, to a lesser extent than does benzalkonium chloride.

Very useful examples of the present preservative components include, but are not limited to oxidative preservative components, for example oxy-chloro components, peroxides, persalts, peracids, and the like, and mixtures thereof. Specific examples of oxy-chloro components useful as preservatives in accordance with the present invention include hypochlorite components, for example hypochlorites; chlorate components, for example chlorates; perchlorate components, for example perchlorates; and chlorite components. Examples of chlorite components include stabilized chlorine dioxide (SCD), metal chlorites, such as alkali metal and alkaline earth metal chlorites, and the like and mixtures therefore. Technical grade (or USP grade) sodium chlorite is a very useful preservative component. The exact chemical composition of many chlorite components, for example, SCD, is not completely understood. The manufacture or production of certain chlorite components is described in McNicholas U.S. Pat. No. 3,278,447, which is incorporated in its entirety herein by reference. Specific examples of useful SCD products include that sold under the trademark Dura Klor® by Rio Linda Chemical Company, Inc., and that sold under the trademark Anthium Dioxide® by International Dioxide, Inc. An especially useful SCD is a product sold under the trademark Purite™ by Allergan, Inc. Other examples of oxidative preservative components includes peroxy components. For example, trace amounts of peroxy components stabilized with a hydrogen peroxide stabilizer, such as diethylene triamine penta(methylene phosphonic acid) or 1-hydroxyethylidene-1,1-diphosphonic acid, may be utilized as a preservative for use in components designed to be used in the ocular environment. Also, virtually any peroxy component may be used so long as it is hydrolyzed in water to produce hydrogen peroxide. Examples of such sources of hydrogen peroxide, which provide an effective resultant amount of hydrogen peroxide, include sodium perborate decahydrate, sodium peroxide and urea peroxide. It has been found that peracetic acid, an organic peroxy compound, may not be stabilized utilizing the present system. See, for example, Martin et al U.S. Pat. No. 5,725,887, the disclosure of which is incorporated in its entirety herein by reference.

Preservatives other than oxidative preservative components may be included in the compositions. The choice of preservatives may depend on the route of administration. Preservatives suitable for compositions to be administered by one route may possess detrimental properties which preclude their administration by another route. For nasal and ophthalmic compositions, preferred preservatives include quaternary ammonium compounds, in particular the mixture of alkyl benzyl dimethyl ammonium compounds and the like known generically as "benzalkonium chloride." For compositions to be administered by inhalation, some preferred preservatives are chlorbutol and the like. Other preservatives which may be used, especially for compositions to be administered rectally, include alkyl esters of p-hydroxybenzoic acid and mixtures thereof, such as the mixture of methyl, ethyl, propyl, butyl esters and the like which is sold under the trade name "Nipastat."

In one broad embodiment, compositions are provided which comprise a TC-EEC complex, a preservative component in an effective amount to at least aid in preserving the compositions and a liquid carrier component. Preferably, the preservative components include oxy-chloro components, such as compounds, ions, complexes and the like which (1) do not substantially or significantly detrimentally affect the TC in the compositions or the patients to whom the compositions are administered, and (2) are substantially biologically acceptable and chemically stable. In one embodiment, compositions in accordance with the present invention comprise a complex of alpha-2-adrenergic agonist-linolenic acid, an oxy-chloro component, and a liquid carrier component, for example, an aqueous component.

The carrier components useful in the present invention are selected to be non-toxic and preferably have no substantial detrimental effect on the present compositions, on the use of the compositions or on the human or animal to whom the compositions are administered. In one embodiment, the carrier component is a liquid carrier. In a preferred embodiment, the carrier component is a liquid carrier component, for example, an aqueous component. A particularly useful liquid carrier component is that derived from saline, for example, a conventional saline solution or a conventional buffered saline solution. The liquid carrier preferably has a pH in the range of about 6 to about 9 or about 10, more preferably about 6 to about 8, and still more preferably about 7.5. The liquid medium preferably has an ophthalmically acceptable tonicity level, for example, of at least about 200 mOsmol/kg, more preferably in the range of about 200 to about 400 mOsmol/kg. In an especially useful embodiment, the osmolality or tonicity of the carrier component substantially corresponds to the tonicity of the fluids of the eye, in particular the human eye. In another useful embodiment, nonionic tonicity components are used.

In one embodiment, the carrier components containing the EECs and the TCs may have viscosities of more than about 0.01 centipoise (cps) at 25° C., for example, more than about 1 cps at 25° C. or, for example, more than about 10 cps at 25° C. In one embodiment, the composition has a viscosity of about 50 cps at 25° C. and comprises a conventional buffer saline solution, a carboxymethylcellulose and a brimonidine tartrate. In one useful embodiment, in place of saline, a non-ionic tonicity component is used.

In order to insure that the pH of the liquid carrier component, and thus the pH of the composition, is maintained within the desired range, the liquid carrier component may include at least one buffer component. Although any suitable buffer component may be employed, it is preferred to select such component so as not to produce a significant amount of chlorine dioxide or evolve significant amounts of gas, such as CO. The buffer component may be inorganic. Alkali metal and alkaline earth metal buffer components are advantageously used in the present invention. For example, phosphate buffers may be used in accordance with the present invention. One or more buffer components may be used in a composition of the present invention.

As used herein, the term "complex" refers to a close association between one or more EECs and one or more TCs. For example, the electrical charge of an TC in solution may maintain one or more EECs comprising an opposite electrical charge in close association. In one embodiment, the present complexes are ion pair complexes in which the electric charge of the EECs and the TC are substantially or even completely balanced. It should be noted, however, that the present invention is not intended to be limited to only such ion pair complexes. Rather, any complex or related combination of EEC(s) and TC component(s) which preferably remain substantially intact in an aqueous environment, and which exhibit one or more of the enhanced effects set forth herein, is to be considered within the scope of the present invention.

The formation of an TC-EEC complex may produce an overall diminishment in the net electrical charge of the TC. To promote the formation of intact TC-EEC complexes, it may be advantageous to provide a relatively large amount of EEC. For example, the ratio of electrical charge from the EEC to electrical charge from the TC may be in the range of about 0.9 to about 1.5, preferably, in the range of about 1.0 to about 1.3. For example, an EEC may have one negative charge per molecule and a TC may have two positive charges per molecule. In this case, a molar ratio of EEC to TC of 2 in a composition will result in a ratio of electrical charge of 1.

In one embodiment, the concentration of EEC in a composition of the invention is less than required to form an emulsion, for example, an EEC/water emulsion in the composition. In other words, the amount of EEC is preferably controlled so that enough EEC is present to complex with substantially all of the TC present, and less EEC is present than that needed to form an emulsion in the composition.

As noted above, high concentrations of ionic species may lower the concentration of intact TC-EEC complexes present in the compositions of the present invention. Conversely, a low concentration of ionic species may increase the concentration of intact TC-EEC complexes. In one embodiment, in order to maintain a low concentration of ionic species, compositions of the present invention include a reduced concentration of buffer component. For example, concentrations of buffer component, for example, phosphate buffer, may be present in compositions of the present invention in an amount in a range of about 0.0001 molar to about 1.0 molar. However, in order to reduce the ionic concentration present in the compositions, the buffer component preferably is present in a concentration in a range of about 0.001 molar to about 0.1 molar or about 0.2 molar, more preferably in a range of about 0.005 molar to about 0.1 molar.

Any suitable ophthalmically acceptable tonicity component or components may be employed, provided that such component or components are compatible with the other ingredients of the liquid carrier component and do not have deleterious or toxic properties which could harm the human or animal to whom the present compositions are administered. In one embodiment, the tonicity component is selected from inorganic salts and mixtures thereof. Examples of useful tonicity components include sodium chloride, potassium chloride, and mixtures thereof.

In order to reduce the ionic concentration of the present compositions, and thereby promote the maintenance of intact EEC-TC complexes, it is preferred that nonionic tonicity components be used in the present compositions. Examples of such nonionic tonicity components include, without limitation, mannitol, dextrose, glycerin, propylene glycol and the like and mixtures thereof.

The present compositions may conveniently be presented as solutions or suspensions in aqueous liquids or non-aqueous liquids, or as oil-in-water or water-in-oil liquid emulsions. The present compositions may include one or more additional ingredients such as diluents, flavoring agents, surface active agents, thickeners, lubricants, and the like, for example, such additional ingredients which are conventionally employed in compositions of the same general type.

The present compositions in the form of aqueous suspensions may include excipients suitable for the manufacture of aqueous suspensions. Such excipients are suspending agents, for example, sodium carboxymethyl-cellulose, methylcellulose, hydroxypropylmethyl-cellulose, sodium alginate, polyvinylpyrrolidone, gun tragacanth and gun acacia; dispersing or wetting agents may be a naturally occurring phosphatide, for example, lecithin, or condensation products of ethylene oxide with long chain aliphatic alcohols, for example, heptadecaethylene-oxycetanol, or condensation products of ethylene oxide with partial esters derived from fatty acids and a hexitol such as polyoxyethylene sorbitol mono-oleate, or condensation products of ethylene oxide with partial esters derived from fatty acids and hexitol anhydrides, for example, polyoxyethylene sorbitan mono-oleate, and the like and mixtures thereof. Such aqueous suspensions may also contain one or more coloring agents, one or more flavoring agents and one or more sweetening agents, such as sucrose, saccharin, and the like and mixtures thereof.

The present compositions in the form of oily suspensions may be formulated in a vegetable oil, for example, olive oil, sesame oil or coconut oil, or in a mineral oil such as liquid paraffin. Such suspensions may contain a thickening agent, for example beeswax, hard paraffin or cetyl alcohol. Sweetening agents, such as those set forth above, and flavoring agents may be added to provide a palatable oral preparation.

The present compositions may also be in the form of oil-in-water emulsions. The oily phase may be a vegetable oil, for example, olive oil or arachis oil, or a mineral oil, for example, liquid paraffin, and the like and mixtures thereof. Suitable emulsifying agents may be naturally-occurring gums, for example, gum acacia or gum tragacanth, naturally-occurring phosphatides, for example, soya bean lecithin, and esters or partial esters derived from fatty acids and hexitol anhydrides, for example, sorbitan mono-oleate, and condensation products of the said partial esters with ethylene oxide, for example, polyoxyethylene sorbitan mono-oleate. The emulsions may also contain sweetening and flavoring agents.

The present compositions in the form of syrups and elixirs may be formulated with sweetening agents, for example, as described elsewhere herein. Such formulations may also contain a demulcent, and flavoring and coloring agents.

The specific dose level for any particular human or animal depends upon a variety of factors including the activity of the active component employed, the age, body weight, general health, sex, diet, time of administration, route of administration, rate of excretion, drug combination and the severity of the particular condition undergoing therapy.

The following non-limiting examples illustrate certain aspects of the present invention.

EXAMPLE 1

Effects of Brimonidine-Linoleic Acid on Intra Ocular Pressure

The data below shows the percent change with time of Intra Ocular Pressure after administration of Brimonidine-linoleic acid at time 0. The treatment is an ion pair formulation of 0.131% Brimonidine and 0.126% linoleic acid.

| | |
|---|---|
| 0 hr | 0.0 mm Hg (administration of complex) |
| 1 hr | −10.4 mm Hg |
| 2 hr | −16.0 mm Hg |
| 4 hr | −9.5 mm Hg |
| 6 hr | −9.4 mm Hg |

EXAMPLE 2

Relative Sedative Effects of Various Compounds

The relative sedative effects of Brimonidine-linoleic acid (compound 65) was compared to saline (compound 62) and Brimonidine tartrate (compound 60). This study involved cross overs and a one-week wash out in between the administration of the various compounds.

As done in a previous experiments, the following method was followed:
1. 6 trained monkeys were placed in chairs and allowed to acclimate for approximately 30 minutes.
2. Individual monkeys were brought into the "testing room" where they were allowed to adjust to the new environment for approximately 2 minutes. After this adjustment time the monkey were observed for 1-2 minutes after which a sedation score was given. Sedation scores were recorded on an observation sheet.
3. The monkey were returned to the group of animals assigned to this study.
4. 2 baseline readings were done at T-0.5 and 0 hour. After the 0 hour reading one drop of the test compound was administered to the right eye.
5. Steps 2 & 3 were repeated at T=0.5, 1, 2, 3 and 4 hour.
6. Animals were monitored until they recover from effects of the drug.
7. Scoring of Sedation was based on the following scale:
   S=0 Monkey is quiet, but slightly active
   S=1 Monkey is quiet, easy to handle for reading
   S=2 Monkey is quiet, relaxed but very low in activity
   S=3 Monkey is blinking eyes and yawning
   S=4 Monkey is sleepy and inactive, eyes are heavy
8. The test compounds were coded: 62-Saline, 65-Brimonidine tortrate, 60-Brimonidine-linoleic acid.
9. Test Compound Administration:

| animal #1 | week 1 | week 2 | week 3 |
|---|---|---|---|
| 19 | 62 | 65 | 60 |
| 24 | 62 | 65 | 60 |
| 42 | 65 | 60 | 62 |
| 50 | 65 | 60 | 62 |
| 57 | 60 | 62 | 65 |
| 58 | 60 | 62 | 65 |

The scoring was conducted for each animal for the different test compounds. The average results are shown on table 1.

TABLE 1

Comparison of the sedative effects of Brimonidine-Linoleic Acid ion pair complex (0.2%) to Brimonidine Tartrate (0.2%) and saline.

| TIME (HR) | SEDATION SCORE |
|---|---|
| Brimonidine-Linoleic Acid Ion Pair Complex | |
| −0.5 | 0.7 |
| 0 | 1.0 |
| 0.5 | 1.2 |
| 1 | 1.5 |
| 2 | 1.8 |
| 3 | 1.6 |
| 4 | 1.6 |
| Brimonidine Tartrate | |
| −0.5 | 0.7 |
| 0 | 0.8 |
| 0.5 | 0.8 |
| 1 | 1.7 |
| 2 | 2.6 |
| 3 | 2.5 |
| 4 | 2.7 |
| Saline Vehicle | |
| −0.5 | 0.7 |
| 0 | 1.0 |
| 0.5 | 1.0 |
| 1 | 1.0 |
| 2 | 1.2 |
| 3 | 1.3 |
| 4 | 1.3 |

The first reading after dosing, 0.5 hr-time point, the monkeys were quiet and easy to handle. In general, the animals started to show low activity when brought into the test room at the 1 hr time.

Half the monkeys given test compound Brimonidine-linoleic showed low activity (1 hour post dose), with the exception of monkey #19. Monkey #19 did not appear to be sleepy, inactive or have heavy eyes and seemed to react similarly to all test compounds. She seems to be very comfortable in the chair, and when there were no distractions she tended to close her eyes and relax.

The dosing with Brimonidine-linoleic acid complex appear to cause more sedation in the monkeys than dosing with saline. In general when the monkeys were dosed with saline, they were quiet and easy to handle for all readings. However, dosing with Brimonidine tartrate causes more sedation than dosing with Brimonidine-linoleic acid. When the monkeys were dosed with Brimonidine tartrate, on average they became sleepy and inactive with heavy eyes. This observation was seen usually at the 2-hour time point and most of the animals remained this way through the end of observations.

Without wishing to limit the invention to any mechanism or theory of operation, it is believed that one of the reasons that Brimonidine-linoleic acid complex causes less sedation than Brimonidine tartrate is that it partitions more in the lipid compartments. In other words, the Brimonidine-linoleic acid complex is more trapped in the lipid compartments, and are not as available to circulate in the blood stream to eventually travel to the brain to cause sedation.

EXAMPLE 3

Effects of Brimonidine-Linoleic Acid Ion Pair Complex (0.2%) on Rabbit Intraocular Pressure In this study, the animals were placed into three groups consisting of a mix of age, size and sex.

| Group Number | Number of Animals Males | Number of Animals Females |
| --- | --- | --- |
| 1 | 4 | 4 |
| 2 | 4 | 4 |
| 3 | 4 | 4 |

One group of animals (both sexes) were used per screening study. The test compound (20 µL of 0.2% Brimonidine-linoleic acid ion pair complex) was administered to the surface of the cornea using an automatic pipette or an appropriate device.

The following general procedure for administering the test compound employed in this study is presented below:
1. Make sure that the 0.25% proparacaine Opthetic® mixture (topical local anesthetic), test compounds, and commercially available treats are available.
2. Turn on the Digilab Modular One™ Pneuma Tonometer (pneumatonometer) [BioRad, Cambridge, Mass.]; it needs approximately 15 minutes to warm up. Turn on gas supply or air pump.
3. Hold probe vertically with the point tip down and press "calibration check" for "zero".
4. Wipe the pneumatonometer probe with an alcohol swab, and inspect the tip membrane for holes.
5. Set the external calibration device (air or water manometer) to 25 mm Hg, place the pneumatonometer probe in the calibration device to an ensure that it corresponded to 25±2 mm Hg.
6. Obtain a rabbit. Make sure the recording data sheets are at hand.
7. Gently restrain the rabbit via a commercial restrainer or a cotton towel. Measure the pupil diameter with the specialized ruler for each eye and record the values on the sheets provided. If the eyes are too dark to obtain a value by this method, a specialized penlight may be used. Obtain a pupil diameter measurement by shining the penlight on the cornea for one second.
8. Slide the upper eyelid up the thumb and visually assess and score the degree of ocular surface redness. Record the value for each eye on the sheet provided.
9. Put one drop of 0.25% proparacaine Opthetic® (50:50 mix of 0.5% proparacaine Opthetic®+Cellufresh®) on the surface of each eye. Wait one or more minutes for ophthetic to take effect.
10. Place the pnematonometer tip on one eye at the site where the curvature of the cornea is greatest. Let the probe shank travel to the black line, not the red line. Persist until a stable reading with the standard deviation below 1.0 is obtained. Repeat the procedure for the contralateral eye. Record the data. (Note: If the animal is upset by the restraint, the reading will be artificially high and cannot be used. Use gentle restraint).
11. At the end of the 0, 6, 24, 30, 48, 54, 72, 78 and 96 hour measurements, use an automatic pipette to apply 20 µL of the test compound to the surface of the cornea of one eye. After the 102 hour measurements, the eyes will be washed out with Refresh® and Prefrin®.
12. Give the animal a treat and return the animal to its cage.
13. Repeat steps 7 to 11 on the remaining animals in the group.

The following general procedure for measuring the effects of the test compound employed in this study is as follows: a reading is conducted at 0, 2, 4, 6, 24, 26, 28, 30, 48, 50, 52, 54, 72, 74, 76, 78, 96, 98, 100, and 102 hours. The pneumatonometer is calibrated before use with a manometer and the probe tip is wiped with an alcohol swab. One drop of 0.25% proparacaine Opthetic®, a corneal anesthetic, is placed on the cornea. Allow sufficient time (approximately 1 minute) for it to anesthetize the cornea before placing the probe on the eye. The eye is gently opened by the person doing the tonometer reading. The probe is placed on the cornea at the point of greatest curvature and a stable reading is obtained. The probe is held parallel to the floor and perpendicular to the line of the rabbit's sight. The reading is repeated until a reasonable reading can be obtained. The piston should be between the red and black lines or at the black line on the probe.

The effects of Brimonidine-linoleic acid ion pair complex is shown on Table 2. It appears that the complex is able to reduce intraocular pressure in a rabbit's eye for at least 6 hours. For example, 6 hours after the administration at times 0 hr, 24 hr, 48 hr, 72 hr, and 96 hr, the intraocular pressure remained below is the initial time. However, it also appears that the effect of the complex is less than 18 hrs. For example, 18 hrs after administration of the complex at time 6 hr, the intraocular pressure returned to about the same initial level.

| TIME (HR) | INTRAOCULAR PRESSURE (mm Hg) |
| --- | --- |
| 0* | 25.8 ± 1.2 |
| 2 | 17.1 ± 1.0 |
| 4 | 21.1 ± 1.0 |
| 6* | 23.9 ± 1.0 |
| 24* | 25.6 ± 0.5 |
| 26 | 19.9 ± 0.6 |
| 28 | 22.9 ± 0.8 |
| 30* | 23.0 ± 1.1 |
| 48* | 26.5 ± 1.0 |
| 50 | 20.4 ± 0.6 |
| 52 | 23.4 ± 0.7 |
| 54* | 24.1 ± 0.8 |
| 72* | 26.8 ± 0.9 |
| 74 | 21.1 ± 0.8 |
| 76 | 23.9 ± 1.1 |
| 78* | 25.2 ± 0.9 |
| 96* | 27.9 ± 1.1 |
| 98 | 20.1 ± 1.3 |
| 100 | 23.9 ± 0.7 |
| 102 | 25.3 ± 1.6 |

*Brimonidine-linoleic acid ion pair were administered at these time points. Values are mean ± S.E.M. n = 8.

EXAMPLE 4

The following composition is prepared by mixing together the specified amounts of the ingredients.

| Ingredient | Amount |
| --- | --- |
| Brimonidine Base | 1.32 mg |
| Linolenic Acid | 1.25 mg |
| 1.0 molar Phosphate Buffer (pH 7.5) | 1.0 ml |
| Polysorbate 80 | 90 mg |
| Purified Water | q.s. to 10 ml |

This composition is formulated for and is effective for the treatment of disorders of the eye.

EXAMPLE 5

The following composition is prepared by mixing together the specified amounts of the ingredients.

| Ingredient | Amount |
| --- | --- |
| Brimonidine Base | 1.32 mg |
| Linolenic Acid | 1.27 mg |
| 1.0 molar Phosphate Buffer (pH 7.5) | 1.0 ml |
| Polysorbate 80 | 90 mg |
| Purified Water | q.s. to 10 ml |

This composition is formulated for and is effective for the treatment of disorders of the eye.

EXAMPLE 6

The following composition is prepared by mixing together the specified amounts of the ingredients.

| Ingredient | Amount |
| --- | --- |
| Brimonidine Base | 1.32 mg |
| Linolenic Acid | 1.25 mg |
| Mannitol | 0.2 g |
| Purified Water | q.s. to 10 ml |

This composition is formulated for and is effective for the treatment of disorders of the eye.

EXAMPLE 7

The following composition is prepared by mixing together the specified amounts of the ingredients.

| Ingredient | Amount |
| --- | --- |
| Brimonidine Base | 1.32 mg |
| Linolenic Acid | 1.25 mg |
| Glycerine | 0.12 g |
| Purified Water | q.s. to 10 ml |

This composition is formulated for and is effective for the treatment of disorders of the eye.

EXAMPLE 8

The following composition is prepared by mixing together the specified amounts of the ingredients.

| Ingredient | Amount |
| --- | --- |
| Brimonidine Base | 1.32 mg |
| Linolenic Acid | 1.25 mg |
| 1.0 molar Phosphate Buffer (pH 7.5) | 0.1 ml |
| Purified Water | q.s. to 10 ml |

This composition is formulated for and is effective for the treatment of disorders of the eye.

EXAMPLE 9

The following composition is prepared by mixing together the specified amount of the ingredients.

| Ingredient | Amount |
| --- | --- |
| Brimonidine Base | 1.32 mg |
| Linolenic Acid | 1.25 mg |
| 1.0 molar Phospate Buffer (pH 7.5) | 1.0 ml |
| Polysorbate 80 | 0.1 mg |
| Purified Water | q.s. to 10 ml |

This composition is formulated for and is effective for the treatment of disorders of the eye.

EXAMPLE 10

The following composition is prepared by mixing together the specified amount of the ingredients.

| Ingredient | Amount |
| --- | --- |
| Brimonidine Base | 1.32 mg |
| Linolenic Acid | 1.25 mg |
| 1.0 molar Phospate Buffer (pH 7.5) | 1.0 ml |
| Polyvinylpyrrolidone | 0.1 g |
| Purified Water | q.s. to 10 ml |

This composition is formulated for and is effective for the treatment of disorders of the eye.

EXAMPLE 11

The following composition is prepared by mixing together the specified amount of the ingredients.

| Ingredient | Amount |
| --- | --- |
| Brimonidine Base | 1.00 mg |
| Linolenic Acid | 1.26 mg |
| 1.0 molar Phosphate Buffer (pH 7.5) | 0.1 ml |
| Polyvinyl Alcohol | 0.1 g |
| Purified Water | q.s. to 10 ml |

This composition is formulated for and is effective for the treatment of disorders of the eye. This composition exemplifies a linolenic acid to brimonidine molar ratio of 2.0 resulting in a ratio of electrical charge from the linolenic acid to electrical charge from the brimonidine of 1.0.

EXAMPLE 12

The following composition is prepared by mixing together the specified amount of the ingredients.

| Ingredient | Amount |
| --- | --- |
| Brimonidine Base | 1.00 mg |
| Linolenic Acid | 1.39 mg |
| 1.0 molar Phosphate Buffer (pH 7.5) | 0.1 ml |
| Poly (oxyethylene) Poly (oxypropylene) Block Polymer | 0.1 g |
| Purified Water | q.s. to 10 ml |

This composition is formulated for and is effective for the treatment of disorders of the eye. This composition exemplifies a linolenic acid to brimonidine molar ratio of 2.2 resulting in a ratio of electrical charge from the linolenic acid to electrical charge from the brimonidine of 1.1.

EXAMPLE 13

The following composition is prepared by mixing together the specified amount of the ingredients.

| Ingredient | Amount |
| --- | --- |
| Brimonidine Base | 1.00 mg |
| Linolenic Acid | 1.51 mg |
| 1.0 molar Phosphate Buffer (pH 7.5) | 0.1 ml |
| Glycerine | 10 mg |
| Polyvinylpyrrolidone | 0.1 g |
| Purified Water | q.s. to 10 ml |

This composition is formulated for and is effective for the treatment of disorders of the eye. This composition exemplifies a linolenic acid to brimonidine molar ratio of 2.4 resulting in a ratio of electrical charge from the linolenic acid to electrical charge from the brimonidine of 1.2.

EXAMPLE 14

The following composition is prepared by mixing together the specified amount of the ingredients.

| Ingredient | Amount |
| --- | --- |
| Brimonidine Base | 1.00 mg |
| Linolenic Acid | 1.64 mg |
| 1.0 molar Phosphate Buffer (pH 7.5) | 0.1 ml |
| Polysorbate 80 | 90 mg |
| Mannitol | 0.2 g |
| Purified Water | q.s. to 10 ml |

This composition is formulated for and is effective for the treatment of disorders of the eye. This composition exemplifies a linolenic acid to brimonidine molar ratio of 2.6 resulting in a ratio of electrical charge from the linolenic acid to electrical charge from the brimonidine of 1.3.

While this invention has been described with respect to various specific examples and embodiments, it is to be understood that the invention is not limited thereto and that it can be variously practiced with the scope of the following claims.

What is claimed is:

1. A liquid composition comprising:
   an ophthalmically acceptable cationic therapeutic component selected from the group consisting of NMDA antagonists, antibacterials, antihistamines, decongestants, antiinflammatories, antiparasitics, miotics, anticholinergics, adrenergics, antivirals, local anesthetics, antifungals, amoebicidals, trichomonocidals, analgesics, mydriatics, antiglaucoma drugs, carbonic anhydrate inhibitors, ophthalmic diagnostic agents, ophthalmic agents used as adjuvants in surgery, chelating agents, antineoplastics, antihypertensives, muscle relaxants, diagnostics, and mixtures thereof in a therapeutically effective amount, and
   an efficacy enhancing component having one, two or three negative charges provided in an amount greater than 0.2% (w/v) and less than about 10% (w/v) and being effective to enhance the pharmacokinetic disposition of the therapeutic component, to enhance the movement of the therapeutic component across a lipid membrane, or a biological membrane under physiological conditions, and to enhance the permeability of the therapeutic component, the efficacy enhancing component being present in an ion pair complex at a molar ratio of 1:3, 1:2, 1:1, 2:1 or 3:1 with the therapeutic component, from about 80% to about 100% of the therapeutic component present in complex with the efficacy enhancing component, the ion-pair complex remaining substantially intact in an aqueous environment, each of the enhanced effects being relative to the effect obtained with the therapeutic component without the efficacy enhancing component; and
   a solubilizer component provided in an amount effective to enhance the solubility of the ion-pair complex in solution.

2. The composition of. claim 1 wherein the therapeutic component is selected from the group consisting of quinoxaline, (2-imidozolin-2-ylamino) quinoxaline, 5-bromo-6-(2-imidozolin-2-ylamino) quinoxaline, and mixtures thereof.

3. The composition of claim 1 wherein the solubilizer component is nonionic.

4. The composition of claim 1 wherein the efficacy enhancing component and the therapeutic component are present in amounts so that a ratio of electrical charge from the efficacy enhancing component to electrical charge from the therapeutic component is at least about 1:1.

5. The composition of claim 1 further comprising an effective amount of a nonionic tonicity component.

6. The composition of claim 1 further comprising an effective amount of a phosphate buffer component in concentration in a range of about 0.001 molar to about 0.1 molar in the composition.

7. A liquid composition comprising:
   an ophthalmically acceptable cationic therapeutic component selected from the group consisting of NMDA antagonists, antibacterials, antihistamines, decongestants, antiinflammatories, antiparasitics, miotics, anticholinergics, adrenergics, antivirals, local anesthetics, antifungals, amoebicidals, trichomonocidals, analgesics, mydriatics, antiglaucoma drugs, carbonic anhydrase inhibitors, ophthalmic diagnostic agents, ophthalmic agents used as adjuvants in surgery, chelating agents, antineoplastics, antihypertensives, muscle relaxants, diagnostics, and mixtures thereof in a therapeutically effective amount;

an efficacy enhancing component having one, two or three negative charges provided in an amount greater than 0.2% (w/v) and less than about 10% (w/v) and being effective to enhance the pharmacokinetic disposition of the therapeutic component, to enhance the movement of the therapeutic component across a lipid membrane, or a biological membrane under physiological conditions, and to enhance the permeability of the therapeutic component, the efficacy enhancing component being present in an ion-pair complex at a molar ration of 3:1, 2:1, 1:1, 1:2 or 1:3 with the therapeutic component, from about 80% to about 100% of the therapeutic component present in complex with the efficacy enhancing component, the ion-pair complex remaining substantially intact in an aqueous environment, each of the enhanced effects being relative to the effect obtained with the therapeutic component without the efficacy enhancing component; and an effective amount of a nonionic tonicity component.

8. The composition of claim 7 wherein the therapeutic component is selected from the group consisting of quinoxaline, (2-imidozolin-2-ylamino) quinoxaline, 5-bromo-6-(2-imidozolin-2-ylamino) quinoxaline, and mixtures thereof.

9. The composition of claim 7 wherein the efficacy enhancing component is selected from the group consisting of anionic polymers, saturated fatty acids and unsaturated fatty acids, and mixtures thereof.

10. The composition of claim 7 wherein the efficacy enhancing component and the therapeutic component are present in amounts so that a ratio of electrical charge from the efficacy enhancing component to electrical charge from the therapeutic component is at least about 1:1.

11. The composition of claim 7 further comprising an effective amount of a phosphate buffer component in a concentration range of about 0.001 molar to about 0.1 molar in the composition.

12. A liquid composition comprising:
an ophthalmically acceptable cationic therapeutic component selected from the group consisting of NMDA antagonists, antibacterials, antihistamines, decongestants, antiinflammatories, antiparasitics, miotics, anticholinergics, adrenergics, antivirals, local anesthetics, antifungals, amoebicidals, trichomonocidals, analgesics, mydriatics, antiglaucoma drugs, carbonic anhydrase inhibitors, ophthalmic diagnostic agents, ophthalmic agents used as adjuvants in surgery, chelating agents, antineoplastics, antihypertensives, muscle relaxants, diagnostics, and mixtures thereof provided in a therapeutically effective amount; and an efficacy enhancing component having one, two, or three negative charges provided in an amount greater than 0.2% (w/v) and less than about 10% (w/v) and being effective to enhance the pharmacokinetic disposition of the therapeutic component, to enhance the movement of the therapeutic component across a lipid membrane, or a biological membrane under physiological conditions, and to enhance the permeability of the therapeutic component, from about 80% to about 100% of the therapeutic component present in complex with the efficacy enhancing component, the efficacy enhancing component being present in an ion-pair complex with the therapeutic component so that a ratio of electrical charge from the efficacy enhancing component to electrical charge from the therapeutic component is at least about 1:1 the complex remaining substantially intact in an aqueous environment, and each of the enhanced effects being relative to the effect obtained with the therapeutic component without the efficacy enhancing component.

13. The composition of claim 12 wherein the therapeutic component is selected from the group consisting of quinoxaline, (2-imidozolin-2-ylamino) quinoxaline, 5-bromo-6-(2-imidozolin-2-ylamino) quinoxaline, and mixtures thereof.

14. The composition of claim 12 wherein the efficacy enhancing component is selected from the group consisting of anionic polymers, saturated fatty acids and unsaturated fatty acids, and mixtures thereof.

15. The composition of claim 12 wherein the complex is not present in an emulsion.

16. The composition of claim 12 wherein the efficacy enhancing component and the therapeutic component are present in amounts so that a ratio of electrical charge from the efficacy enhancing component to electrical charge from the therapeutic component is in a range of about 1.1 to about 1.5.

17. The composition of claim 12 further comprising an effective amount of a phosphate buffer component in a range of about 0.01 molar to about 0.1 molar in the composition.

18. A liquid composition comprising:
an ophthalmically acceptable cationic therapeutic component selected from the group consisting of NMDA antagonists, antibacterials, antihistamines, decongestants, antiinflammatories, antiparasitics, miotics, anticholinergics, adrenergics, antivirals, local anesthetics, antifungals, amoebicidals, trichomonocidals, analgesics, mydriatics, antiglaucoma drugs, carbonic anhydrase inhibitors, ophthalmic diagnostic agents, ophthalmic agents used as adjuvants in surgery, chelating agents, antineoplastics, antihypertensives, muscle relaxants, diagnostics, and mixtures thereof in a therapeutically effective amount;

an efficacy enhancing component comprising a fatty acid provided in an amount greater than 0.2% (w/v) and less than about 10% (w/v) and being effective to enhance the pharmacokinetic disposition of the therapeutic component, to enhance the movement of the therapeutic component across a lipid membrane, or a biological membrane under physiological conditions, and to enhance the permeability of the therapeutic component; the efficacy enhancing component being present in an ionpair complex at a molar ratio of 1:3, 1:2, 1:1, 2:1 or 3:1 with the therapeutic component; from about 80% to about 100% of the therapeutic component present in complex with the efficacy enhancing component(s); the complex remaining substantially intact in an aqueous environment; and each of the enhanced effects being relative to the effect obtained with the therapeutic component without the efficacy enhancing component.

* * * * *